Figure 1:
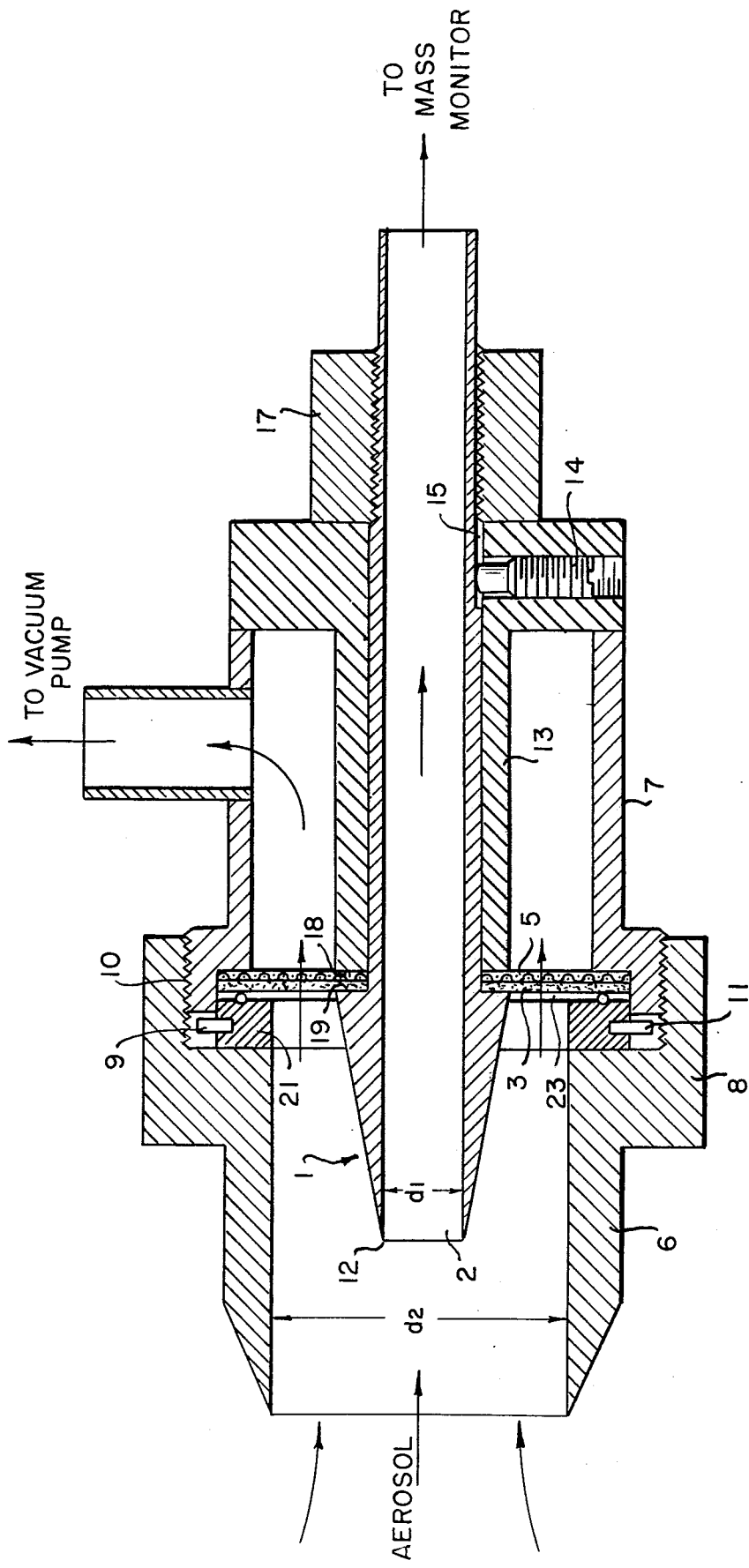
Figure 2:
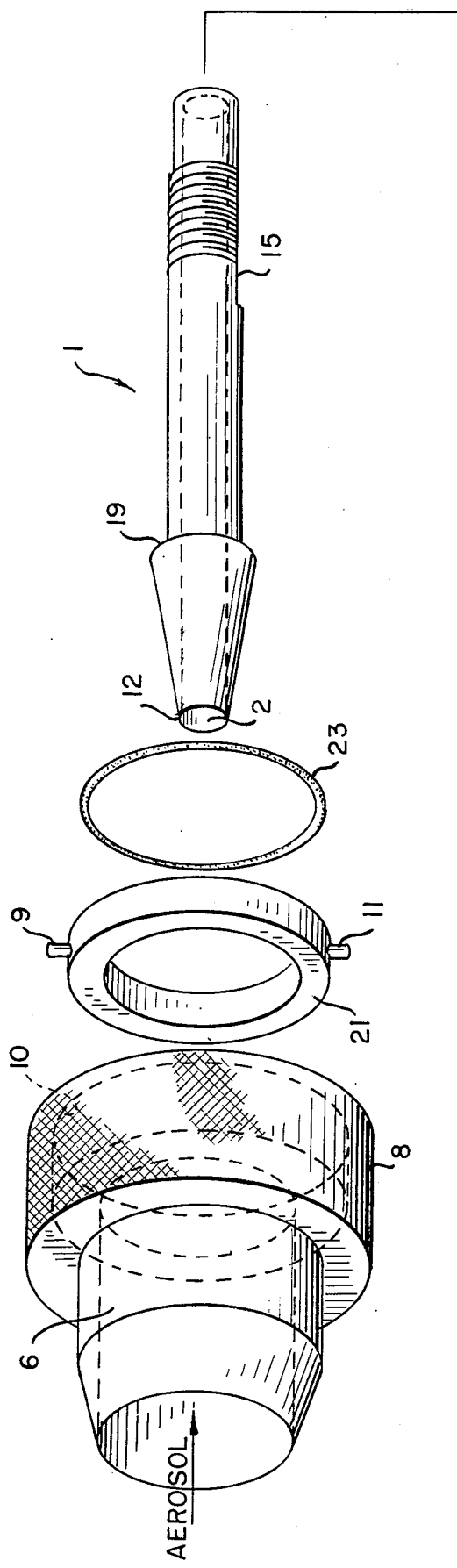
Figure 2:
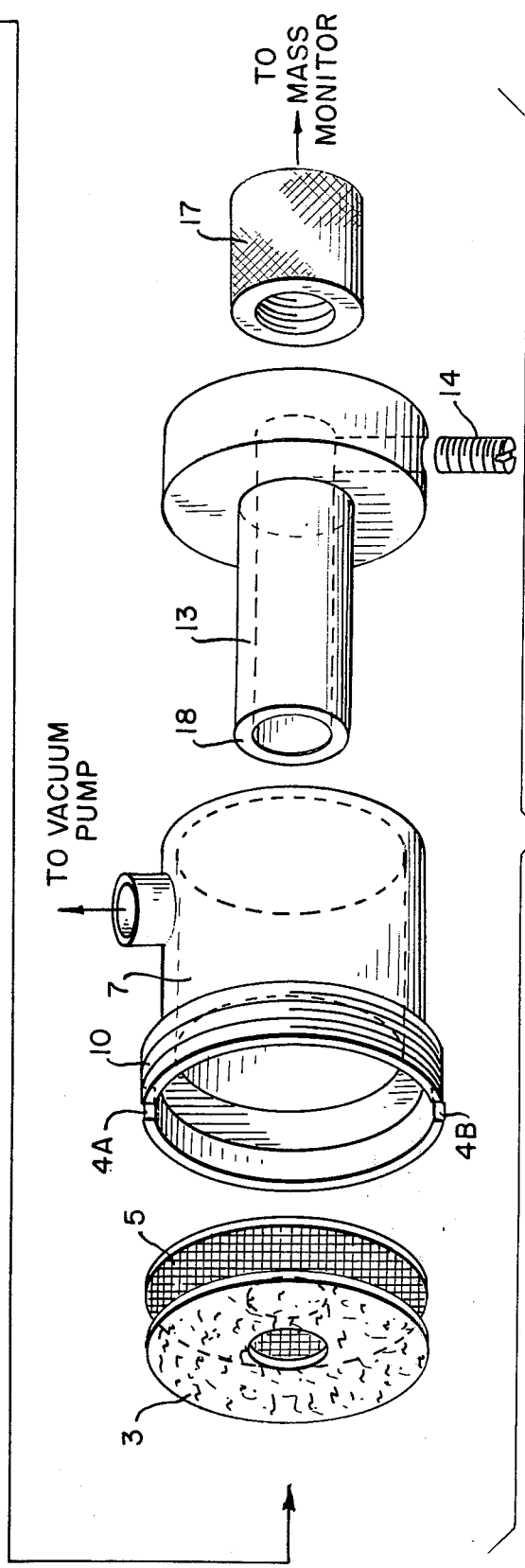

United States Patent [19]  [11] 3,954,428
Marple et al.  [45] May 4, 1976

[54] PRECISION AEROSOL DIVIDER

[75] Inventors: Virgil A. Marple, Plymouth; Kenneth T. Whitby, Golden Valley, both of Minn.

[73] Assignee: The United States of America as represented by the Secretary of the Interior, Washington, D.C.

[22] Filed: July 28, 1975

[21] Appl. No.: 599,741

[52] U.S. Cl. .................................. 55/270; 55/17; 55/307; 73/28; 210/433 M
[51] Int. Cl.² ............................................. B01D 46/00
[58] Field of Search ............... 55/17, 270, 307, 308, 55/423, 478, 480; 73/28, 421.5 A, 421.5 R; 210/433 R

[56] References Cited
UNITED STATES PATENTS

| | | |
|---|---|---|
| 3,261,199 | 7/1966 | Aaynor .................................. 73/28 |
| 3,518,815 | 7/1970 | McFarland et al. .............. 55/270 X |
| 3,528,279 | 9/1970 | Lassred et al. ..................... 55/270 X |

*Primary Examiner*—John Adee
*Attorney, Agent, or Firm*—Thomas Zack; Donald R. Fraser

[57] ABSTRACT

A precision aerosol divider used primarily as a calibration device for a mass monitor instrument. The divider is made up of a filter holder with an isokinetic probe in the center that is connected to the inlet of the monitoring instrument. This type of arrangement provides for a flow split by a fixed ratio of the incoming aerosol stream into the filter and mass monitor. A special filter clamping device minimizes the disturbance of the deposit thereon by preventing rotation of the filter. Two pins in a filter retaining ring located between two sections of the holder body act to provide this clamping function.

7 Claims, 3 Drawing Figures

PRECISION AEROSOL DIVIDER

BACKGROUND OF THE INVENTION

1. Field of the Invention

The invention described in this specification relates to a precision aerosol divider.

2. Description of the Prior Art

When it was previously desired to calibrate aerosol mass concentration instruments usually a dust box or wind tunnel was used in the operation. A filter in the box or tunnel retained the sampled particles. The deficiency with these types of sampling devices is that difference of air velocity and inlet sizes at the mass sampling instrument input and the filter result in sampling efficiencies differences.

Another method used to calibrate mass monitoring instruments is to pass the aerosol through a common passage and then split the flow at a "Y" in the line. Each leg of the "Y" went to a different instrument — one to the filter and one to the mass monitor. Generally, the split must be nearly 1 to 1 to ensure that the aerosol mass split is the same as the flow split and that the particle size distribution has not been altered. In addition to this limitation, where gravimetric measurements on the filter are being used as the standard, experience has shown it is more desirable to have the flow through the filter substantially larger than through the mass monitoring instrument. Our invention almost totally eliminates or substantially reduces these deficiencies of the prior art by using an isokinetic probe that is centered in the filter as will be explained hereafter.

SUMMARY OF THE INVENTION

The precision aerosol divider is made up of a sectioned filter holder body, a filter, and an isokinetic conduit probe that extends through the approximate center line of the holder. The filter is held so that it extends between the hollow of the body and the probe body and is retained there by a clamping device constituting part of its holder. The aerosol flow may be such that the portion going to the center of the holder has it outlet flow — directly to a mass monitor and the outlet portion going through the filter is pumped by a vacuum pump.

The primary object of this invention is an improved aerosol divider.

BRIEF DESCRIPTION OF THE DRAWINGS

FIG. 1 is a cross-sectional of the assembled preferred embodiment of our invention.

FIG. 2 is an exploded perspective view of the FIG. 1 embodiment.

FIG. 3 shows a typical calibration set up using our invention.

As shown in FIG. 1 the preferred embodiment consists of an isokinetic probe 1, an annular filter 3, and a filter support. The hollow tubular shaped holder has an upper body section 6 that is threaded to a lower body section 7 with an outer filter clamping ring 8 therebetween. Threads 10, which extend completely around the joining surfaces of the upper and lower sections, rigidly maintain the holder together when tightened. Associated with the clamping ring are two oppositely directed pins 9 and 11 on ring 21 that prevent this ring from rotating with respect to the lower body section. These locking pins are inserted in the slots 4A and 4B of the threaded upper portion of body member 7.

When tightened the ring 8 bears down on the filter via the annular gasket ring 21. A flexible O ring 23 may also be added. The ring retaining pins prevent the frictional contact between the clamping ring and upper section from being imparted as a rotational effect to the filter as the upper body section is loosened or tightened.

The tubular isokinetic probe has a center hole 2 or aerosol flow conduit extending its entire length in the longitudinal direction. At the upper end of the probe facing in the direction of aerosol flow is a sharp edge 12 which acts to split the aerosol flow stream between the hole 2 and the holder cavity with the filter. One working embodiment had a ratio flow split of 17 to 1 meaning that 17 times more aerosol by volume flows through the filter per unit time than through the center hole 2. The particular ratio is fixed by the ratio of the probe's passageway diameter *d*1 to the uniform diameter of body inlet designed by the letter *d*2. Variations are, of course, possible in this ratio by varying either of these diameters although it is usually the probe's diameter *d*1 that is varied. One assumption as to the operation of our invention should be mentioned, namely that the velocity profile in the aerosol divider will remain flat and experience little or no turbulent flow when split. Such an assumption can be made since the distance from the inlet of the aerosol divider to the inlet of the isokinetic probe is short in comparison to the dimension *d*2, and thus the boundary layer close to the inner walls of the upper body section will be small.

The lower section of the holder has an upright tubular section 13 fixed thereto which acts to assist in holding and centering the probe within the holder. A threaded pin 14 extends through a similarly threaded hole in a lower body section and provides a locating point for a keyway slot 15 near the lower end of the isokinetic probe 1, preventing the probe's rotation. The probe's itself is also generally tubular in shape except for the keyway slot near the lower end and the upper tapered end above the filter. This upper probe end can be described as being frusto conical in cross-section with a center hole. The lower horizontal lip 19 of this end overlaps and bears against the filter's upper surface to hold the filter between it and the horizontal top surface of upright 13. The lower end of the probe nearest the mass monitor is threaded so that a restraining nut 17 engages it and the lower surface of lower section 7. Upon tightening this arrangement draws the probe downward to securely fasten the probe to the holder's upright center body support 13. Thus, it should be clear that it is the combination of the upright 13, the threaded pin 14, the restraining nut 17, and the probe lip 19 which act together to rigidly hold the probe.

The annular filter has a center hole to receive the probe and extends completely across the cavity between the curved parallel walls formed by the outer side of upright 13 and the inner wall of lower section 7. The filter material is a material which exhibits a minimum of moisture pickup and remains intact throughout the clamping and unclamping process. One filter found satisfactory was a cellulose filter membrane having a 0.8 micron pore sizes. Other materials and pore sizes may also be used.

FIG. 2 is an exploded perspective view of the FIG. 1 preferred embodiment. From this, it can be seen that the tubular probe 1 with its frusto-conical upper end has a circular edge 12 thereon. It also has a lower slot 15 and a center hole 2. This probe fits into and on the tubular upright 13 to hold the filter 3 and filter support 5 therebetween at their outer edges as previously described. The two sets of threads 10 — one on the section 7 and one on the inner side of ring 8 — act to hold the filter and its support as well as the rings 21 and 23. The probe itself is held by the nut 14 in the probe's slot 15 and the nut 17 which pulls the probe's lip 19 against the annular top edge 18 of upright support 13 with the filter's inner edge therebetween. All of these parts of the filter holder have been made of brass but other materials such as aluminum or stainless steel could also be used.

Figure 3:
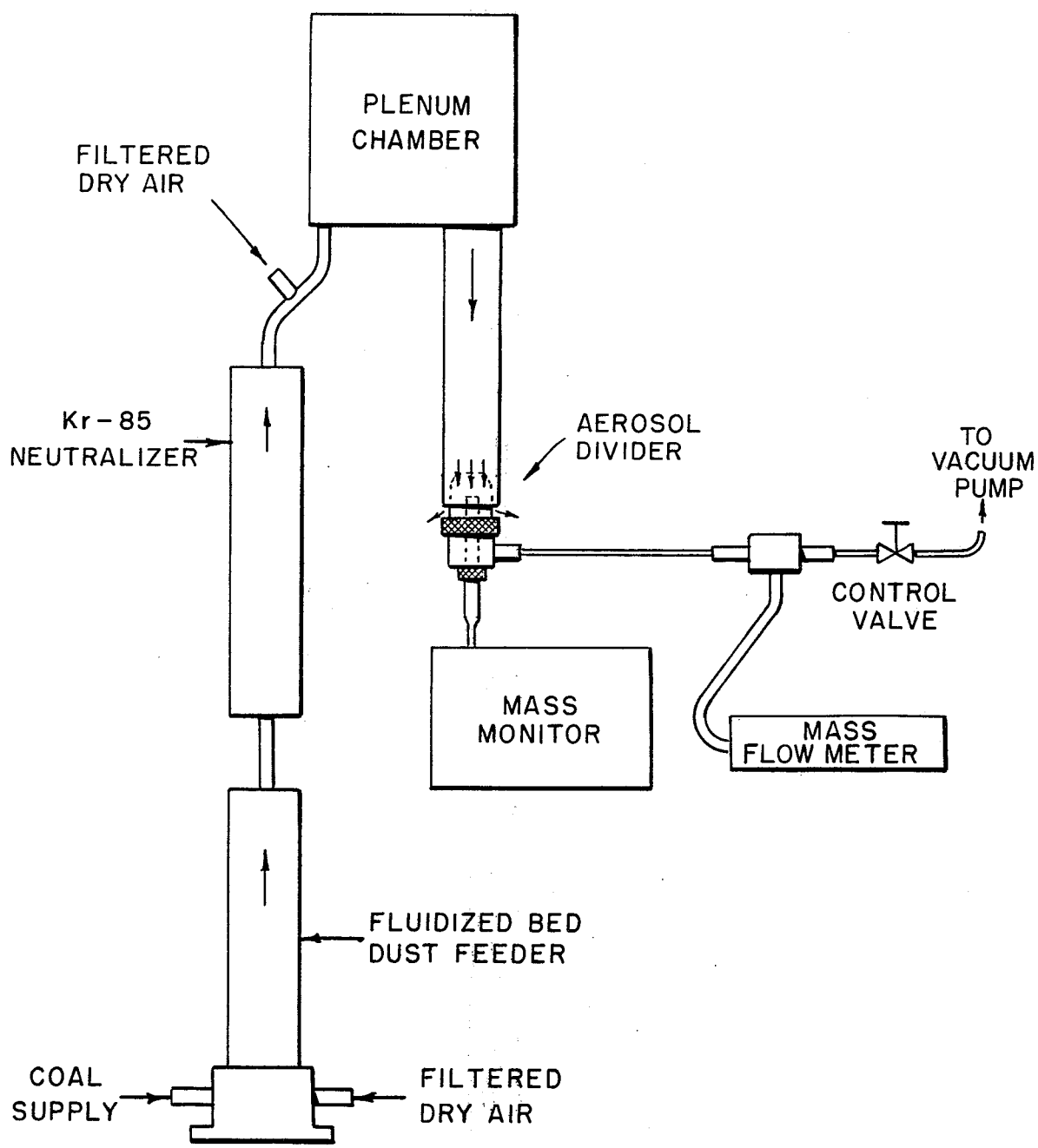

FIG. 3 is a calibration system set up using our aerosol divider. In the working embodiment used the aerosol divider had a 17 to 1 flow split, a central probe with an inner diameter of 0.818 centimeters (cm); an inlet inner diameter of 3.46 cm and a 47 millimeter (mm) (0.8 micron pore size) filter with a 1.51 cm center diameter hole for the probe. Starting at the lower left hand side of FIG. 3, coal dust is generated in a fluidized bed feeder by combining coal and filtered dry air. It is then passed through a Kr — 85 neutralizer which acts to electrically neutralize the coal particles. Thereafter, the dust passes into a plenum chamber where, at its entrance, additional clean dry air is mixed with the dust to make a flow rate slightly higher than that required by the aerosol divider. From the plenum the aerosol passes directly to the aerosol divider through a tube which is slightly larger than the inlet of the aerosol divider.

In our working model the flow rate through the annular filter is monitored by a hot wire mass flow meter which is insensitive to pressure. A mass flow meter was used instead of a volumetric flow meter because of an appreciable pressure drop through the annular divider filter. When the filter becomes loaded with coal dust, the pressure drop is increased necessitating the adjustment of the shown flow control valve during the operation.

The Mass monitor that was caibrated was a GCA Respirable dust monitor model RDM 101-1 (GCA Corporation, GCA Technology Division, Bedford, Mass. 01730). As such it is a beta attenuation device which collects the particles on the impaction plate of an impactor. Typically the flow of aerosol is about 2 liters per minute (1pm) to the monitor with the mass of collected particles varying in the $10^{-6}$ ($\mu$e) gram (gm) range.

To weigh the mass of particles collected on the mass monitor and aerosol divider filters a Perkins-Elmer Auto AD-1 balance was used. This instrument has an accuracy of $\pm$ 0.1 $\mu$e gm for weights less than 1 miligram (mgm). Varying humidity effects on the filter weights may be cancelled by using the difference in weight between the actual filter used and a reference filter of the same material by placing the reference filter on the counterbalance pan of the balance. In addition this difference in weight basis keeps the weight measurements to less than 1 mgm. To neutralize any charge that may be on the filters a radioactive source was placed next to the balance pans. A further refinement was to carry out all calibrations in a special constant temperature room and to allow all filters to equalibrate to the same conditions as the tare filter.

Using fixed values of 0.818 cm and 3.46 cm for $d1$ and $d2$ respectfully, nine tests were made to calibrate the mass monitoring instrument with an embodiment of our invention. For variating flow rates splits the following table I indicates the results of these tests:

Table I

| Test | Aerosol Division Tests | | | |
|---|---|---|---|---|
| | Mass Collected on Annular Filter (34 lpm) | Mass Collected on Filter at Mass Monitor Probe (2 lpm) | Aerosol Mass Split Ratio | Average Concentration |
| 1 | 4029 $\mu$gm | 248 $\mu$g | 16.2:1 | 3.2 $\mu$g/l |
| 2 | 3116 | 183 | 17.0:1 | 2.5 |
| 3 | 2623 | 162 | 16.2:1 | 2.1 |
| 4 | 3362 | 217 | 15.5:1 | 4.9 |
| 5 | 6653 | 373 | 17.8:1 | 8.4 |
| 6 | 602 | 37 | 16.3:1 | 0.4 |
| 7 | 5170 | 305 | 17.0:1 | 4.8 |
| 8 | 1949 | 127 | 15.3:1 | 0.8 |
| 9 | 1195 | 245 | 17.1:1 | 3.1 |
| | | Average | 16.5:1 | |

Standard deviation = 0.8 from 17:1 ratio
Standard deviation = 4.8 percent

From the above table it can be concluded that the average aerosol mass split ratio is within 3 percent of the desired 17:1 ratio and there is a 4.8 percent standard deviation. Also to be noted is that the aerosol mass split ratio is independent of the mass concentration at which the test was made.

This invention has several advantages over the prior art. First, it accurately splits the aerosol into two streams to allow for accurate calibration of a mass aerosol monitor by preserving the particle size distribution in its original form. Second, the split ratio can be varied over a wide range of values by changing the diameter of the isokinetic probe. Thirdly, the simplicity of its design and ease of use insures that the particle size distribution and concentration will be unaffected by the splitting of the aerosol flow into two streams and that there will be a minimum of particle loss between the point where the aerosol flow is split and where the particles are collected on the filter or sampled by the mass monitoring instrument.

None of the specific features described with respect to the preferred embodiment should be used to limit the scope and extent of our invention which is to be measured only by the claims that follow.

We claim:

1. A precision aerosol divider comprising:

a hollow filter holder body having an inlet for an aerosol flow and a first and second flow outlet, said holder body also having means for holding a probe upright approximately in the center of the holder to thereby connect said inlet to the first of said two outlets;

an isokinetic hollow probe with a center passageway insertable in said means for holding a probe, said probe having an upper edge facing the inlet to split the aerosol flow;

a small probe filter with a large center hole held between said probe and holder body to receive the flow stream to the second of said two outlets after it is split by the probe's edge.

2. The divider of claim 1 also comprising additional probe retaining means for rigidly fastening said probe to the holder body.

3. The divider of claim 1 wherein said holder body comprises an upper and lower disassemble section with said filter being held between these sections.

4. The divider of claim 3 also including two filter retaining pins to engage said holder's body and a retaining ring that bears against said filter, thereby allowing the removable of said filter from the holder's body without rotating the filter.

5. The divider of claim 4 wherein said means for holding a probe upright has an upper bearing surface that engages the lower surface of the filter near its center, the probe being inserted within the filter's hole to bear against its upper surface and thereby retain the filter.

6. The divider of claim 1 wherein said probe has an upper and lower section with said passageway extending throughout its length completely through said sections, said upper section being frustoconical shaped in cross-section and said lower section being generally cylindrical in shape.

7. The divider of claim 1 wherein the flow split ratio is determined by the ratio of the holder body inlet and the probe's center passageway.

* * * * *